US007974686B2

(12) United States Patent
Lee et al.

(10) Patent No.: US 7,974,686 B2
(45) Date of Patent: Jul. 5, 2011

(54) MULTI-CHANNEL BIO-MED ELECTRIC SIGNALS CAPTURING DEVICE BASED ON A SOUND SIGNAL GENERATION

(75) Inventors: Chao-Fa Lee, Taipei (TW); Shih-Jung Chang, Taipei (TW); Cheng-Hsing Kuo, Taipei (TW)

(73) Assignee: Tatung Company, Taipei (TW)

( * ) Notice: Subject to any disclaimer, the term of this patent is extended or adjusted under 35 U.S.C. 154(b) by 264 days.

(21) Appl. No.: 12/379,476

(22) Filed: Feb. 23, 2009

(65) Prior Publication Data
US 2010/0160803 A1   Jun. 24, 2010

(30) Foreign Application Priority Data

Dec. 23, 2008 (TW) ................. 97150189 A

(51) Int. Cl.
*A61B 5/04* (2006.01)
(52) U.S. Cl. ...................................................... 600/509
(58) Field of Classification Search .................. 600/383, 600/509, 407, 508
See application file for complete search history.

(56) References Cited

U.S. PATENT DOCUMENTS

| 3,690,313 A | * | 9/1972 | Weppner et al. ............... 600/508 |
| 4,710,865 A | * | 12/1987 | Higomura ........................ 700/63 |
| 2005/0239047 A1 | * | 10/2005 | Gimzewski et al. .............. 435/4 |
| 2010/0059274 A1 | * | 3/2010 | Ives et al. ..................... 174/71 R |

* cited by examiner

*Primary Examiner* — George Manuel
*Assistant Examiner* — Robert N Wieland
(74) *Attorney, Agent, or Firm* — Bacon & Thomas, PLLC

(57) ABSTRACT

A multi-channel bio-med electric signals capturing device includes: a detection channel unit, a control unit, a voice signal generator and a computer device. The detection channel unit is provided to detect bioelectric signals produced from human body and amplify the same. The control unit is provided to capture the amplified bio-med electric signals based on a frequency conforming to a computer acceptable audient signal. The voice signal generator transmits the captured amplified bio-med electric signals to a microphone of the computer device, whereby a recording program built in the computer device records the input audient signal as a voice file. Accordingly, the user is able to monitor the bio-med electric signals by easily and simply using a computer device.

7 Claims, 3 Drawing Sheets

MULTI-CHANNEL BIO-MED ELECTRIC SIGNALS CAPTURING DEVICE BASED ON A SOUND SIGNAL GENERATION

BACKGROUND OF THE INVENTION

1. Field of the Invention

This invention relates with a generally multi-channel bio-med signals capturing device and a sound signal generator. Multi-channel bio-med signals are conveyed out a sound signal.

2. Description of Related Art

Many physiological monitoring parameters are range of low frequency level. For example, the capturing frequency of electrocardiogram is within a certain range from 0.01 Hz to 200 Hz frequency. Others bio-med electric signals, such as electroencephalography (EEG), Electrogasfrogrm (EGG) and pulse wave, are lower than 200 Hz. Currently, the human bio-med electric signals were measured usually use an analog-to-digital conversion device to transform captured analog signals to change the computer acceptable signals. However, using digital system to interpret bio-med electric signals is complicated in technical application. The user could hardly handle these digital signals. Further, transforming captured bio-med electric signals to digital signals is constrained to transfer rate and required equipment that don't accord with and be not suitable for user's habit. If users only need for examining whether daily physiological value is in regular condition or not, the use of the human bio-med electric signals measurement device to detect physiological value seems to be too complicated. Therefore, it is desired to provide a multi-channel bio-med electric signals capturing device for users to easily operate with computer recording program to record bio-med electric signals as a voice file in daily life.

SUMMARY OF THE INVENTION

The object of the present invention is to provide a multi-channel bio-med electric signals capturing device for user easily operating with computer recording program to record bio-med electric signals as a voice file in daily life.

To achieve the object, there is provided a multi-channel bio-med electric signals capturing device comprising: a computer device having a microphone input; one or more detection channel unit having a detection circuit and a signal amplifying circuit, wherein the detection circuit detects bio-med electric signals produced from human body and transmits the bio-med electric signals to the signal amplifying circuit; a control unit including a main controller, a multiplexer and a pulse generator, the main controller being electrically connected to the mutiplexer and the pulse generator, the multiplexer being electrically connected to the signal amplifying circuits, wherein the main controller commands the mutiplexer to capture the bio-med electric signals amplified by the signal amplifying circuits according to capturing frequency generated by the pulse generator and conforming to a computer acceptable audient signal by the voice signal generator; and a voice signal generator including an analog switch and a connection interface, the connection interface being connected to the microphone input of the computer device, the analog switch being connected to the signal amplifying circuits and the multiplexer, whereby the amplified bio-med electric signals captured by the multiplexer according to the capturing frequency are transmitted to the microphone input of the computer device through the connection interface; wherein the computer device records the signals conforming to the computer acceptable audient signal and saved as a voice file.

Other objects, advantages, and novel features of the invention will become more obviously from the following detailed description when taken in conjunction with the accompanying drawings.

BRIEF DESCRIPTION OF TV DRAWINGS

DETAILED DESCRIPTION OF THE PREFERRED EMBODIMENT

Figure 1:
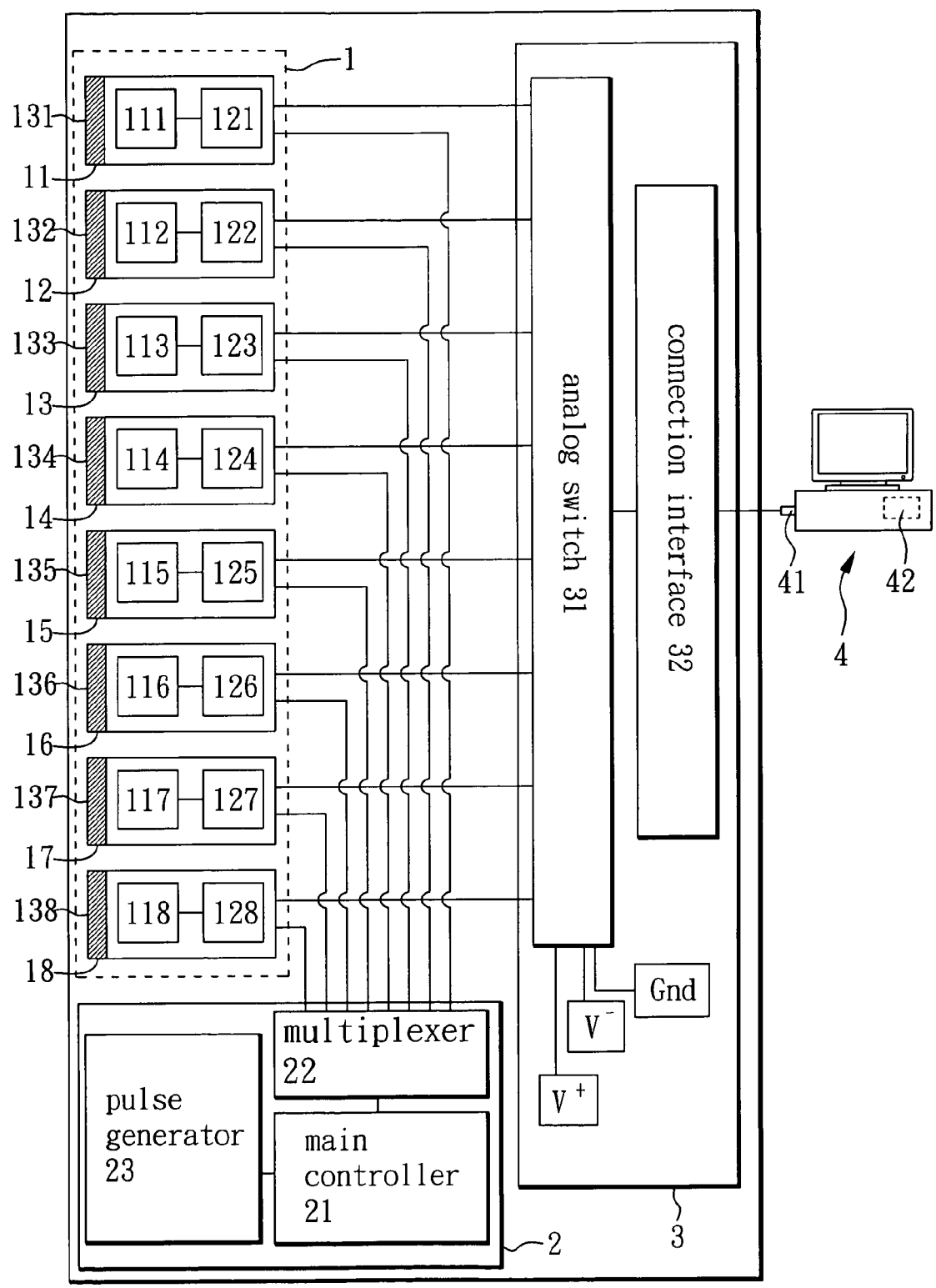
FIG. 1 is a perspective view of a system diagram of a multi-channel bio-med electric signals capturing device in accordance with the present invention.

FIG. 1 shows a system diagram of a multi-channel bio-med electric signals capturing device in accordance with the present invention, which comprises a detection channel unit 1, a control unit 2, a voice signal generator 3 and a computer device 4. The detection channel unit 1 includes multiple detection channels, such as a first detection channel 11, a second detection channel 12, a third detection channel 13, a fourth detection channel 14, a fifth detection channel 15, a sixth detection channel 16, a seventh detection channel 17 and an eighth detection channel 18. The first detection channel 11 has a first detection circuit 111 and a first signal amplifying circuit 121. The first detection circuit 111 is electrically connected to the first signal amplifying circuit 121. Similarly, the inner circuit arrangements of detection channels 12-18 are the same with that of the first detection channel 11, including detection circuits 112-118 and signal amplifying circuits 121-128, the detection circuits 112-118 being electrically connected to the signal amplifying circuits 121-128. The detection channel unit 1 is used to attach to a proper position on human skin for detecting bio-med electric signals sourced from human body. The detection channels 11-18 have outer isolating layers 131-138 respectively to protect human skin from an electric shock caused by inner circuit leakage.

The aforementioned control unit 2 includes a main controller 21, a multiplexer 22 and a pulse generator 23. The main controller 21 is electrically connected to the multiplexer 22 and the pulse generator 23. The multiplexer 22 is electrically connected to the signal amplifying circuits 121-128. The voice signal generator 3 includes an analog switch 31 and a connection interface 32. The analog switch 31 is connected to the signal amplifying circuits 121-128 and the multiplexer 22. The analog switch 31 is provided with a set of reference voltages (V+, V− and Gnd) be used as reference points of a start signal, the amplified bio-med electric signals captured respectively, and an end signal. A computer acceptable audient signal could be constructed by a voice signal generator 3. The computer device 4 is preferred to be a personal computer, including a microphone input 41 and a recording program 42. The microphone input 41 is electrically connected to the connection interface 32. The recording program 42 records the voice signal, which is inputted at the microphone input 41, as a voice file.

Figure 2:
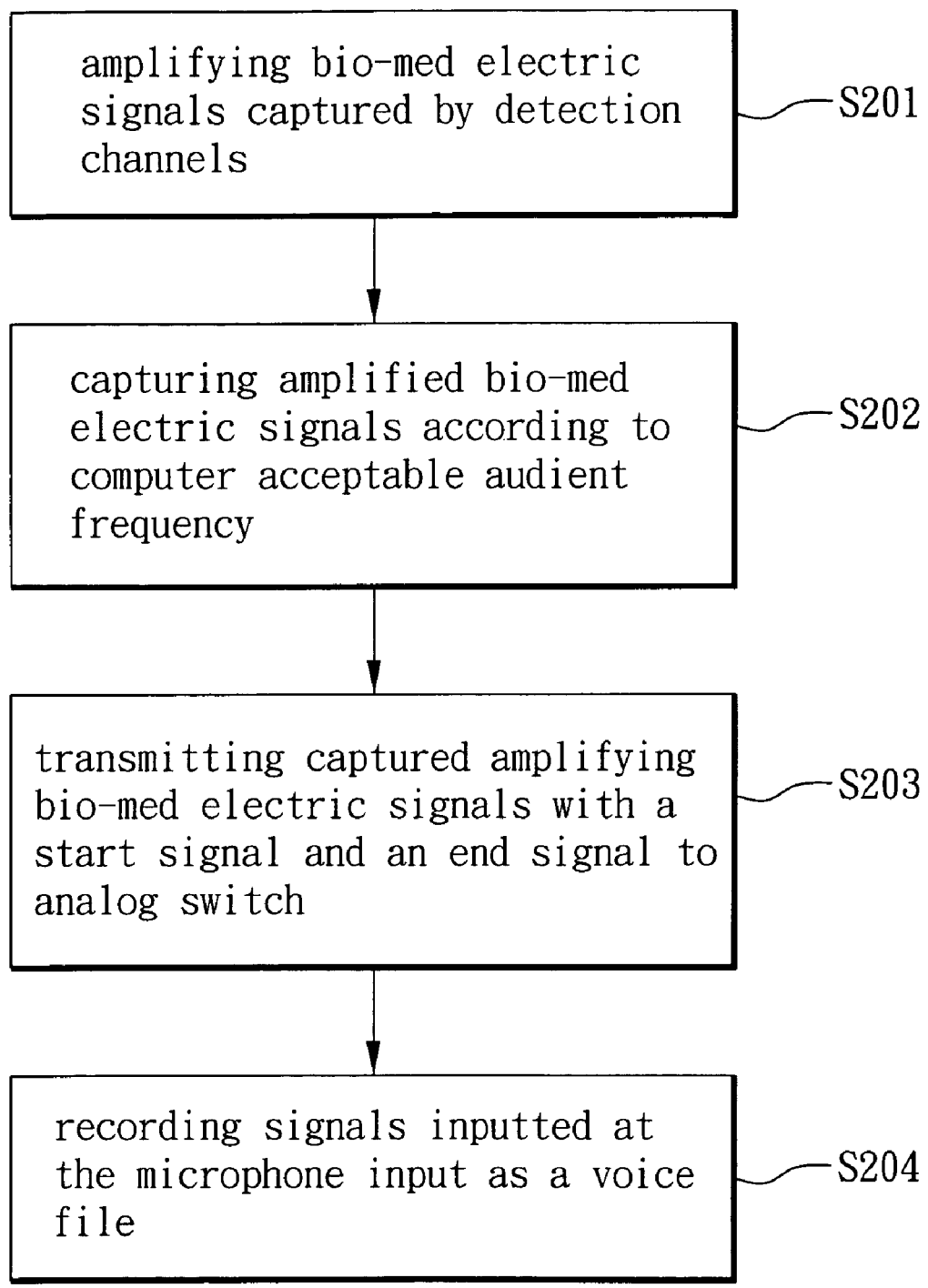
FIG. 2 is a flowchart showing the operation of the multi-channel bio-med electric signals capturing device in accordance with the present invention.
Figure 3:
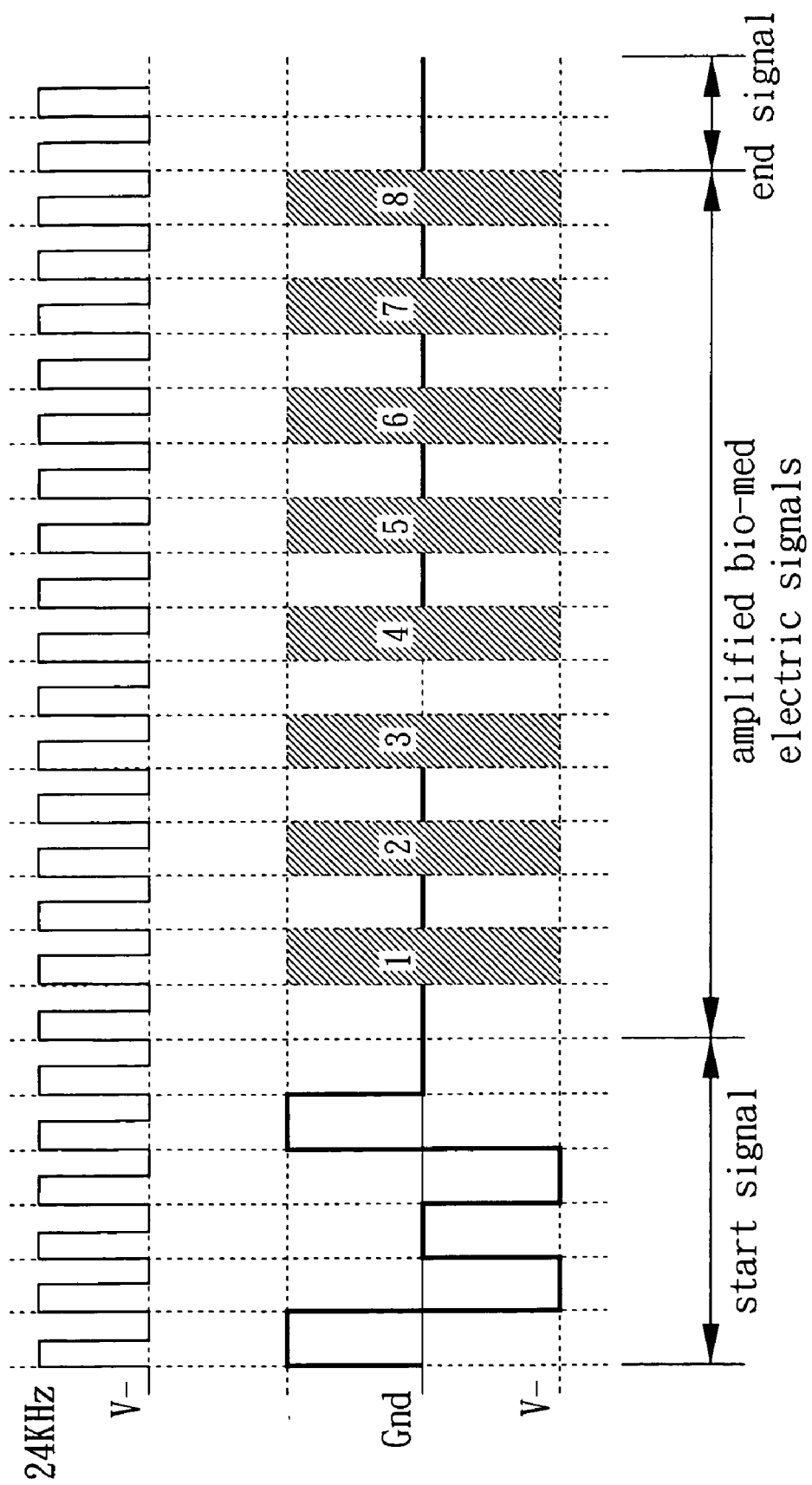
FIG. 3 is an output waveform of captured signals in accordance with the preferred embodiment.

FIG. 2 is a flowchart showing the operation of the multi-channel bio-med electric signals capturing device in accordance with the present invention. Firstly, the eight detection channels 11-18 are provided to detect eight kinds of bio-med electric signals sourced from human body respectively and amplify those signals (step 201). For example, the first detection circuit 111 of the first detection channel 11 detects EEG from the skin of scalp, the second detection circuit 112 of the second detection channel 12 detects ECG from human extremities, the third detection circuit 113 of the third detection channel 13 detects pulse wave of vessel flow, and the fourth detection circuit 114 of the fourth detection channel 14 detects EGG from abdomen. These bio-med electric signals are transmitted to the signal amplifying circuits 121-128 for signal amplification. Then, the amplified bio-med electric signals are sequentially captured by the multiplexer 22 controlled by the main controller 21 according to the capturing frequency which is generated by the pulse generator 23 and conforms to a computer acceptable audient signal (step 202). Next, these captured amplified bio-med electric signals together with a start signal and an end signal are transmitted to the analog switch 31 that has a set of reference voltage (V+, V− and Gnd) for use as reference points of output signals (step 203). For instance, if a computer acceptable audient frequency of the this embodiment is 48 KHz, it is able to design a capturing model that uses 24 KHz as based frequency and 1 KHz as capturing frequency; that is, each based frequency has twenty-four captured signals. The capturing model of this preferred embodiment configures previous six signals, which are V+, V−, Gnd, V−, V+, Gnd, as the start signal according to the reference voltages of analog switch 31. The capturing model then distributes eight Gnd voltages and eight signals captured by the detection channels 11-18 as middle sixteen signals, which are Gnd, amplified bio-med electric signal of first detection channel, Gnd, amplified bio-med electric signal of second detection channel, Gnd, amplified bio-med electric signal of third detection channel, Gnd, amplified bio-med electric signal of fourth detection channel, Gnd, amplified bio-med electric signal of fifth detection channel, Gnd, amplified bio-med electric signal of sixth detection channel, Gnd, amplified bio-med electric signal of seventh detection channel, Gnd, and amplified bio-med electric signal of eighth detection channel. Finally, the capturing model configures the last two signals, which are Gnd and Gnd, as the end signal. These captured signals are transmitted to the analog switch 31. An output waveform of the captured signals is shown as FIG. 3. After transmitting to the analog switch 31, these captured signals are transmitted to the microphone input 41 of the computer device 4 through the connection interface 32, and recorded as a voice file by the recording program 42.

Although the present invention has been explained in relation to its preferred embodiment, it is to be understood that many other possible modifications and variations can be made without departing from the scope of the invention as hereinafter claimed.

What is claimed is:

1. A multi-channel bio-med electric signals capturing device, comprising:
 a computer device having a microphone input;
 a detection channel unit including plural detection channels, each said detection channel having a detection circuit and a signal amplifying circuit, wherein the detection circuit detects bio-med electric signals produced from human body and transmits the bio-med electric signals to the signal amplifying circuit for signal amplification;
 a control unit including a main controller, a multiplexer and a pulse generator, the main controller being electrically connected to the mutiplexer and the pulse generator, the multiplexer being electrically connected to the signal amplifying circuits, wherein the main controller commands the mutiplexer to capture the bio-med electric signals amplified by the signal amplifying circuits according to capturing frequency generated by the pulse generator and conforming to a computer acceptable audient signal; and
 a voice signal generator including an analog switch and a connection interface, the connection interface being connected to the microphone input of the computer device, the analog switch being connected to the signal amplifying circuits and the multiplexer, whereby the amplified bio-med electric signals captured by the multiplexer according to the capturing frequency are transmitted to the microphone input of the computer device through the connection interface;
 wherein the computer device records the signals conforming to the computer acceptable audient signal and inputted at the microphone input as a voice file.

2. The multi-channel bio-med electric signals capturing device of claim 1, wherein the plural detection channels of the detection channel unit are provided to detect different bio-med electric signals respectively.

3. The multi-channel bio-med electric signals capturing device of claim 1, wherein each detection channel has an outer isolating layer to protect human skin from a shock of inner circuit leakage.

4. The multi-channel bio-med electric signals capturing device of claim 1, wherein the analog switch is provided with a set of reference voltages (V+, V− and Gnd) for use as reference points of a start signal, the amplified bio-med electric signals captured respectively, and an end signal.

5. The multi-channel bio-med electric signals capturing device of claim 1, wherein the bio-med electric signals detected by the detection circuits include brain wave, cardiac wave, pulse wave and gastrointestinal wave.

6. The multi-channel bio-med electric signals capturing device of claim 1, wherein the computer device has a recording program to record the inputted signals as a voice file.

7. The multi-channel bio-med electric signals capturing device of claim 6, wherein the computer device is a personal computer.

* * * * *